United States Patent [19]

Sarges et al.

[11] 4,181,729
[45] Jan. 1, 1980

[54] PHENYL OR PHENOXY SUBSTITUTED SPIRO-IMIDAZOLIDINEDIONE DERIVATIVES

[75] Inventors: Reinhard Sarges, Mystic, Conn.; John L. Belletire, Madison, Wis.

[73] Assignee: Pfizer Inc., New York, N.Y.

[21] Appl. No.: 22,400

[22] Filed: Mar. 21, 1979

[51] Int. Cl.² .............. A61K 31/415; C07D 491/10; C07D 495/10; C07D 235/02
[52] U.S. Cl. .................. 424/273 R; 548/308; 548/307; 548/314; 260/590 FA
[58] Field of Search .............. 548/309, 314, 308; 424/273 R

[56] References Cited

U.S. PATENT DOCUMENTS

| 2,716,648 | 8/1955 | Jules et al. | 548/308 |
|---|---|---|---|
| 2,872,454 | 2/1959 | Shaw | 548/314 |
| 3,532,744 | 10/1970 | Fletcher et al. | 548/308 |
| 3,821,383 | 6/1974 | McKenna et al. | 424/258 |
| 4,117,230 | 9/1978 | Sarges | 548/309 |
| 4,127,665 | 11/1978 | Sarges et al. | 424/273 R |
| 4,130,714 | 12/1978 | Sarges | 548/309 |

FOREIGN PATENT DOCUMENTS 1135915  9/1962  Fed. Rep. of Germany ........... 548/309

OTHER PUBLICATIONS

Gotthardt et al. Chem. Abst. 1977, vol. 86, No. 89689C.

*Primary Examiner*—Natalie Trousof
*Attorney, Agent, or Firm*—F. X. Murphy; C. J. Knuth; A. J. Nelson

[57] ABSTRACT

Novel phenyl or phenoxy substituted spiro-imidazolidinedione derivatives useful as aldose reductase inhibitors and as therapeutic agents for the treatment of chronic diabetic complications are disclosed. The derivatives include the phenyl or phenoxy substituted spiro-imidazolidine naphthalene, chroman, thiochroman sulfoxychroman, sulfonochroman dione compounds and the substituted forms thereof.

7 Claims, No Drawings

PHENYL OR PHENOXY SUBSTITUTED SPIRO-IMIDAZOLIDINEDIONE DERIVATIVES

BACKGROUND OF THE INVENTION

This invention relates to novel phenyl or phenoxy substituted imidazolidinedione derivatives and their pharmaceutical preparations which are useful in the treatment of certain chronic complications arising from diabetes mellitus, such as diabetic cataracts and neuropathy.

Although many oral antidiabetic agents, such as the sulfonyl ureas, effectively lower blood sugar levels, the prevention or alleviation of the chronic complications of diabetes, such as diabetic cataracts, neuropathy, retinopathy and nephropathy has proved harder to achieve. According to the U.S. Pat. No. 3,821,383, aldose reductase inhibitors such as 1,3-dioxo-1H-benz[-d,e]-isoquinoline-2(3H)-acetic acid and its derivatives are useful in this regard. Spiro-hydantoin or imidazolidinedione compounds are also aldose reductase inhibitors and are described in U.S. Pat. Nos. 4,117,230, 4,130,714 and 4,127,665. Such compounds inhibit the enzymatic reduction of aldoses, such as glucose to the corresponding polyols, such as sorbitol, thus preventing or reducing the harmful and unwanted accumulations of polyols in the lens and retina of the diabetically cataractous eye, in the diabetically neuropathic peripheral nerve and in the diabetically nephropathic kidney.

SUMMARY OF THE INVENTION

The compounds of the present invention are phenyl or phenoxy substituted spiro-imidazolidinedione derivatives of formulas I and II

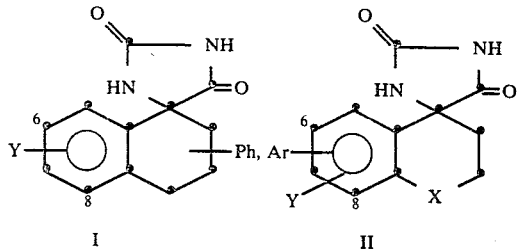

and the pharmaceutically acceptable metal salts thereof wherein X is O, S, SO or $SO_2$; Y is H, $CH_3$, $CH_3O$, Ph, PhO, F, Cl or Br at the 6 or 8 position and Ar is Ph or OPh at the 6 or 8 position. Preferred embodiments include:

1',2',3',4'-tetrahydro-3'-phenyl-spiro-[imidazolidine-4,4'-naphthalene]-2,5-dione of formula I wherein Y is H and Ph is at the 3 position;

1',2',3',4'-tetrahydro-1'-phenyl-spiro-[imidazolidine-4,4'-naphthalene]-2,5-dione of formula I wherein X is H and Ph is at the 1 position;

6'-phenyl-spiro[imidazolidine-4,4'-chroman]-2,5-dione of formula II wherein X is O, Y is H and Ar is Ph at the 6 position;

8'-phenyl-spiro[imidazolidine-4,4'-chroman]-2,5-dione of formula II wherein X is O, Y is H and Ar is Ph at the 8 position;

6'-phenoxy-spiro[imidazolidine-4,4'-chroman]-2,5-dione of formula II wherein X is O; Y is H and Ar is PhO at the 6 position;

8'-chloro-6'-phenyl-spiro[imidazolidine-4,4'-chroman]-2,5-dione of formula II wherein X is O, Y is Cl at the 8 position and Ar is Ph at the 6 position.

The present invention includes a method of treating a diabetic host to inhibit harmful, in vivo enzymatic reduction of aldoses or to prevent or alleviate diabetes associated complications, such as cataracts, neuropathy, nephropathy or retinopathy. This treatment is accomplished by administering to the host a therapeutic amount of the derivative of formula I. Also included is a pharmaceutical preparation of a pharmaceutically-acceptable carrier and a derivative in a therapeutic amount for inhibiting harmful, in vivo enzymatic reduction of aldoses or preventing or alleviating diabetes-associated complications.

DETAILED DESCRIPTION OF THE INVENTION

The phenyl or phenoxy substituted imidazolidinedione derivatives are readily prepared from the appropriate ketones of formulas III and IV

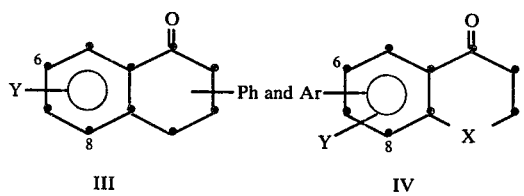

The ketone is condensed with an alkali metal cyanide such as sodium or potassium cyanide, and ammonium carbonate in the presence of a reaction-inert polar organic solvent in which both the reactants and reagents are mutually miscible. Preferred organic solvents include cyclic ethers such as dioxane and tetrahydrofuran, lower alkylene glycols such as ethylene glycol and trimethylene glycol, water-miscible lower alkanols such as methanol, ethanol and isopropanol, and N,N-di(-lower alkyl)lower alkanamides such as N,N-dimethyl formamide, N,N-diethyl formamide and N,N-dimethyl acetamide. In general, the reaction is conducted at a temperature from about 50° C. to about 150° C., preferably about 90° C. to 130° C., for a period of about 2 hours to about 4 days, depending on the temperature employed. Although the reactant and reagents should be employed in the reaction in at least a stoichiometric amount, it is preferable to employ a moderate molar excess of the alkali metal cyanide and ammonium carbonate reagents with respect to the ketone in order to achieve maximum yield. Upon completion of the reaction, the desired product is readily isolated using conventional techniques. For example the reaction mixture may be diluted with water and the resultant aqueous solution cooled to room temperature, followed by acidification to afford the desired deriative.

The ketones are known and readily available or can be prepared by methods known to those skilled in the art. Examples are given below.

The pharmaceutically acceptable metallic salts can be readily prepared from the corresponding unneutralized derivatives using conventional methods. Treatment of a derivative with an aqueous solution of the desired pharmaceutically acceptable metallic hydroxide or other metallic base and evaporation of the resulting solution to dryness, preferably under reduced pressure, will afford the salt. Alternatively, a lower alkanol solution of a derivative may be mixed with an alkoxide of the desired metal followed by evaporation of the alcohol solvent. The pharmaceutically acceptable metallic hydroxides, bases and alkoxides include those with cations that form metallic salts with the acidic, unneutralized derivative and that are nontoxic at the dosages administered to a subject in need of treatment. Suitable cations include potassium, sodium, ammonium, calcium and magnesium.

The derivatives are of therapeutic value in the prophylactic and remedial treatment of chronic complications of diabetes, such as cataracts, retinopathy, nephropathy and neuropathy. They may be administered to a subject in need of treatment by a variety of conventional routes of administration, such as oral, intravenous, intramuscular, subcutaneous, topical, opthalmic and intraperitoneal. In general, they will be administered at dosages between 1 and 250 mg per kg body weight of the subject to be treated per day. However, the particular dose, formulation and route of administration depend upon each patient's unique condition and the judgment of his attending physician.

The derivatives may be administered alone or in combination as a pharmaceutical preparation using a pharmaceutically acceptable carrier such as inert solid diluents, aqueous solutions or various nontoxic organic solvents in dosage forms such as gelatin capsules, tablets, powders, lozenges, syrups, injectable solutions and the like. The carriers include water, ethanol, gelatins, lactose, starches, vegetable oils, petroleum jelly, gums, glycols, talc, benzyl alcohols and other known ingredients for medicaments. If desired, these pharmaceutical preparations may contain auxiliary material such as preserving agents, wetting agents, stabilizing agents, lubricating agents, absorption agents, buffering agents and isotonic agents.

The ability of the derivatives to control chronic diabetic complications may be determined by a number of standard biological or pharmacological tests. These include (1) measuring the ability to inhibit the enzyme activity or isolated aldose reductase; (2) measuring the ability to reduce or inhibit sorbitol accumulation in the sciatic nerve of acutely streptozotocinized (i.e., diabetic) rats; (3) measuring the ability to reverse already-elevated sorbitol levels in the sciatic nerve and lens of chronic streptozocin-induced diabetic rats; (4) measuring the ability to prevent or inhibit galactitol formation in the lens of acutely galactosemic rats; and (5) measuring the ability to delay cataract formation and reduce the severity of lens opacities in chronic galactosemic rats.

The present invention is exemplified by the preparation of several derivatives and by their biological activities in tests 1 and 2 above. It will be understood, however, that the invention is not limited to the specific details given.

General Procedure for Synthesis of the Derivatives

The phenyl or phenoxy substituted spiro-imidazolidinedione derivatives exemplified in Table I were synthesized from the appropriate ketone using the following general preparation procedure.

About 4 g of the ketone, 1 to 3 g of potassium cyanide, 9 to 10 g of ammonium carbonate and 40 to 50 ml ethanol were heated at about 120° C. in a steel bomb for 15 to 20 hours. The reaction mixture was cooled, diluted with about 150ml water and acidified with concentrated hydrochloric acid to precipitate the derivative. It was washed with water and recrystallized from ethanol to yield the purified derivative. The derivatives prepared and their characterizing data are listed in Table 1.

The derivatives of formula II wherein X is SO or $SO_2$ may also be prepared from the corresponding derivative wherein X is S by oxidation with one or two equivalents of meta-chloroperbenzoic acid in methylene chloride.

Table 1
Some Examples of the derivatives and their physical characterizing data

| Example | Derivative | m.p.(°C.) | | Analysis C | H | (1. calculated) (2. found) N |
|---|---|---|---|---|---|---|
| 1 | 1',2',3',4'-tetrahydro-3'-phenyl-spiro[imidazolidine-4,4'-naphthalene]-2,5-dione | 286-9 | $(CH_{18}H_{16}N_2O_2)$ | 1. 73.95  2. 73.85 | 5.52  5.52 | 9.59  9.54 |
| 2 | 1',2',3',4'-tetrahydro-1'-phenyl-spiro[imidazolidine-4,4'-naphthalene]-2,5-dione | 210-12 | $(C_{18}H_{16}N_2O_2)$ $(\frac{1}{2}H_2O)$ | 1. 72.89  2. 72.79 | 5.52  5.66 | 9.45  9.79 |
| 3 | 6'-phenyl-spiro[imidazolidine-4,4'-chroman]-2,5-dione | 283-5 | $(C_{17}H_{14}N_2O_3)$ | 1. 69.37  1. 69.21 | 4.79  4.99 | 9.52  9.45 |
| 4 | 8'-phenyl-spiroimidazolidine-4,4'-chroman]-2,5-dione | 217-18.5 | $(C_{17}H_{14}N_2O_3)$ | 1. 29.38  2. 69.06 | 4.80  5.03 | 9.52  9.09 |
| 5 | 6'-phenoxy-spiro[imidazolidine-4,4'-chroman]-2,5-dione | 168 | $(C_{17}H_{14}N_2O_4)$ | 1. 65.80  2. 65.81 | 4.55  4.51 | 9.03  8.89 |
| 6 | 8'-chloro-6'-phenyl-spiro-[imidazolidine-4,4'-chroman]-2,5-dione | 243-4 | $(C_{17}H_{13}ClN_2O_3)$ | 1. 62.11  2. 61.77 | 3.99  4.08 | 8.52  8.19 |

Preparation of the Ketones

The ketones of formulas III and IV may be prepared using procedures analogous to those given by the references of Table 2. In addition the procedures given below may be used to prepare ketones of formula IV. The sulfoxide and sulfone ketones of formula IV wherein X is SO or $SO_2$ may also be prepared from the corresponding sulfide by oxidation with meta-chloroperbenzoic acid.

Preparation of 6-phenoxy-4-chromanone (Used in Example 5)

3-(p-Phenoxyphenoxy)propionitrile was prepared by heating under reflux for 18 hours a mixture of 25 g of p-phenoxyphenol, 28.4 g of acrylonitrile and 5 ml of a 40% solution of benzyltrimethylammonium hydroxide in methanol. It was worked up by cooling, diluting with 400 ml water, extracting using ethyl acetate; washing the organic layer with 5% aqueous sodium hydroxide, drying, evaporating the solvent, and recrystallizing from hexane to yield 11.1 g of 3-(p-phenoxyphenoxy)-propionitrile m.p. 81-3° C.

The nitrile (11 g) was hydrolyzed by refluxing for 1.5 hours in 100 ml formic acid, 100 ml concentrated hydrochloric acid. The solution was then diluted with 1500 ml of water to precipitate 10.5 g of the corresponding propionic acid m.p. 114-6° C.

The acid (10.3 g) was cyclized by dissolving it in polyphosphoric acid (110 g) and heating on a steam bath for 13 minutes. It was worked up by diluting with 700 ml ice/water, filtering the precipitate, dissolving the precipitate in ethyl acetate, washing with aqueous sodium bicarbonate, drying, evaporating the solvent and recrystallizing from hexane to yield 9.0 g of 6-phenoxy-4-chromanone m.p. 58-60° C.

Preparation of 6-phenyl-4-chromanone (Used in Example 6)

3-(2-chloro-4-phenylphenoxy)propionic acid m.p. 158-9° C., was prepared following the above procedure.

The acid (2 g) was cyclized by allowing it to stand in 20 ml anhydrous hydrogen fluoride at ambient temperature for 24 hours. It was worked up by diluting with water, extracting with chloroform, washing the organic layer with aqueous sodium bicarbonate, drying and evaporating the solvent to yield 1.3 g of low melting 6-phenyl-4-chromanone.

Table 2

| Used in Example | Known Ketones | |
|---|---|---|
| | Ketone | Literature Reference |
| 1 | 2-phenyl-3,4-dihydro-1 (2H) naphthalenone | J. Am. Chem. Soc., 76 1641 (1954) |
| 2 | 4-phenyl-3,4-dihydro-1(2H) naphthalenone | Acta. Chem. Scand. 12, 967 (1958) |
| 3 | 6-phenyl-4-chromanone | CA: 49, 14746g |
| 4 | 8-phenyl-4-chromanone | CA: 51, P9708c |

Aldose Reductase Inhibitory Activity

The derivatives prepared in Examples 1-6 were tested for their ability to reduce or inhibit aldose reductase enzyme activity, following the procedure described in U.S. Pat. No. 3,821,383 and based on the procedure of Hayman et. al., Journal of Biological Chemistry, 240, 877 (1965). The substrate employed was partially purified aldose reductase enzyme obtained from calf lens. The drug was tested to determine the concentration that would cause 50 percent inhibition of enzyme activity.

| Derivative Example | 50% Inhibitory Concentration (Molar) |
|---|---|
| 1 | greater than $10^{-4}$ |
| 2 | $10^{-4}$ |
| 3 | less than $10^{-4}$ |
| 4 | $10^{-6}$ |
| 5 | $10^{-5}$ |
| 6 | $10^{-5}$ |

Inhibition of Sorbitol Accumulation

Some of the Examples of derivatives prepared above were also tested for their ability to reduce or inhibit sorbitol accumulation in the sciatic nerve of streptozotocinized (i.e., diabetic) rats essentially by the procedure described in U.S. Pat. No. 3,821,383. In the present study, the amount of sorbitol accumulation in the sciatic nerves was measured 27 hours after induction of diabetes. The compounds were administered orally at the dose level indicated at 4, 8 and 24 hours following the administration of streptozotocin. The results obtained in this manner are presented in terms of percent inhibition (%) afforded by the test compound compared to the control where no compound was administered (i.e., the untreated animal where sorbitol levels normally rise from approximately 50-100 mM/g tissue to as high as 400 mM/g tissue in the 27-hour test period).

| Derivative Example | % Inhibition at Dose (mg./kg. t.i.d.) |
|---|---|
| 1 | 18% at 25 |
| 2 | 27% at 25 |
| 3 | 0% at 1.5 |
| 4 | 54% at 10 |
| 5 | 0% at 1.5 |
| 6 | not tested |

We claim:
1. A phenyl or phenoxy substituted spiroimidazolidinedione derivative selected from the group consisting of

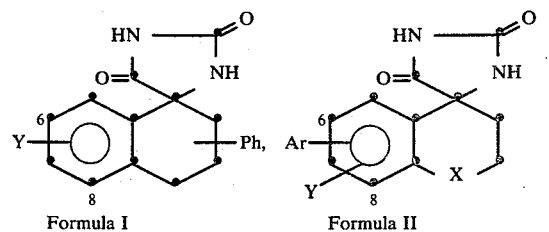

Formula I    Formula II and the pharmaceutically acceptable metallic salts thereof, wherein:

X is O, S, SO or $SO_2$; Y is H, $CH_3$, $CH_3O$, Ph, PhO, F, Cl or Br at the 6 or 8 position; and Ar is Ph or OPh at the 6 or 8 position.

2. The derivative of formula I of claim 1 wherein Y is H, and Ph is at the 1 or 3 position.

3. The derivative of formula II of claim 1 wherein X is O, Y is H and Ar is Ph at the 6 or 8 position.

4. The derivative of formula II of claim 1 wherein X is O, Y is H and Ar is PhO at the 6 position.

5. The derivative of formula II of claim 1 wherein X is O, Y is Cl at the 8 position and Ar is Ph at the 6 position.

6. A pharmaceutical preparation for inhibiting harmful, in vivo enzymatic reduction of aldoses or preventing or alleviating diabetes associated complications, which comprises:
a pharmaceutically acceptable carrier and
a therapeutic amount of a derivative of claim 1.

7. A method of treating a diabetic host to inhibit harmful, in vivo enzymatic reduction of aldoses or to prevent or alleviate diabetes associated complications, which comprises: administering to the host a therapeutic amount of a derivative of claim 1.

* * * * *